United States Patent [19]

Stein

[11] Patent Number: 5,345,612
[45] Date of Patent: Sep. 13, 1994

[54] SURGICAL GLOVE

[76] Inventor: Daniel T. Stein, 2415 Buckeye St., Newport Beach, Calif. 92660

[21] Appl. No.: 35,504

[22] Filed: Mar. 22, 1993

Related U.S. Application Data

[63] Continuation of Ser. No. 823,261, Jan. 21, 1992, abandoned.

[51] Int. Cl.$^5$ ............................................. A41D 13/10
[52] U.S. Cl. ....................................................... 2/168
[58] Field of Search ............. D2/21, 163, 161 R, 168, D2/16, 159, 160, 161.6, 161.7

[56] References Cited

U.S. PATENT DOCUMENTS

| | | | |
|---|---|---|---|
| 1,066,480 | 7/1913 | Finlay | D2/163 X |
| 2,847,012 | 8/1958 | Eastman | 128/303 |
| 3,290,695 | 12/1966 | Burtoff | D2/161 R |
| 3,633,216 | 1/1972 | Schonholtz | D2/168 |
| 4,094,014 | 6/1978 | Schroeder | D2/161 R |
| 4,507,807 | 4/1985 | Karkanen | 2/161 |
| 4,864,661 | 9/1989 | Gimbel | D2/168 X |
| 4,873,998 | 10/1989 | Joyner | D2/16 X |
| 4,901,372 | 2/1990 | Pierce | D2/167 |
| 4,924,530 | 5/1990 | Tagaya | 2/163 |
| 4,995,119 | 2/1991 | Codkind | D2/163 |
| 5,070,543 | 12/1991 | Beck | D2/163 |
| 5,088,124 | 2/1992 | Dutchik | D2/163 |

FOREIGN PATENT DOCUMENTS

| | | | |
|---|---|---|---|
| 0120668 | 9/1979 | Japan | D2/LD2 168 |
| 0672876 | 1/1990 | Switzerland | D2/168 |
| 809741 | 3/1959 | United Kingdom | D2/168 |
| 2224634 | 5/1990 | United Kingdom | D2/159 |

*Primary Examiner*—Clifford D. Crowder
*Assistant Examiner*—Sara M. Current
*Attorney, Agent, or Firm*—Price, Gess & Ubell

[57] ABSTRACT

An improved surgical glove is provided having reinforcing pads formed over the distal finger and thumb pulps and over the metacarpal-phalangeal joints. The fingertips and thumb tips are the most likely region of a surgical glove to be accidentally penetrated by a needle during a surgical procedure. Furthermore, the fingertips, thumb tips, and metacarpal-phalangeal region of the surgical glove are the most likely portions of the glove to become abraded and possibly torn during a surgical procedure. Thus, the reinforcing pads are optimally located for minimizing the possibility of a tear or a needle penetration. The remaining portions of the surgical glove are of conventional thickness and flexibility, thereby assuring adequate mobility of the fingers and hand, such that precise surgical procedures may be performed while using the improved glove.

1 Claim, 7 Drawing Sheets

SURGICAL GLOVE

This is a continuation of application Ser. No. 07/823,261, filed on Jan. 21, 1992, for a Surgical Glove, now abandoned.

BACKGROUND OF THE INVENTION

1. Field of the Invention

The invention relates to an improved surgical glove and to a method for making the improved glove.

2. Description of Related Art

With the advent of AIDS (Acquired Immune Deficiency Syndrome), medical practitioners, particularly surgeons, may be at increased risk during surgical operations. Conventional surgical gloves are provided primarily to maintain adequate sterilization of a surgical area, and are not durably fabricated for protection against needles or other sharp instruments and body parts such as splintered bones. Thus, during any surgery or medical operation requiring the use of sharp implements such as a needle, there is a considerable risk of accidental penetration or laceration of the surgical glove, with the most common area of laceration being along the fingertips and thumb tip. An accidental needle penetration is particularly dangerous, since the needle will likely not only penetrate the surgical glove, but the physician's finger or thumb as well. Further, a conventional surgical glove may become abraded or torn, particularly along the knuckles and fingertips, during a procedure. In either circumstance, a communicable disease, such as AIDS, may be transmitted from the patient to the physician.

Accordingly, there is a need to provide an improved surgical glove that is sufficiently durable to function without the risk of tearing and sufficiently reinforced to prevent accidental penetration or laceration.

SUMMARY OF THE INVENTION

Accordingly, it is an object of the invention to provide an improved surgical glove.

It is a further object of the invention to provide a surgical glove which is sufficiently durable to withstand a lengthy medical procedure without tearing, yet sufficiently flexible to allow the surgeon unhindered use of his or her hand and fingers during the operation.

It is a further object of the invention to provide a surgical glove which is both durable and flexible, yet has sufficient interior volume to avoid hand fatigue and numbness.

It is a further object of the invention to provide methods for manufacturing an improved surgical glove.

These and other objects of the invention are achieved by the provision of an improved surgical glove formed from a thin flexible material such as latex of generally uniform thickness, but having reinforcing pads provided along volar sides of distal ends of the glove thumb and glove fingers.

In accordance with a preferred embodiment, the reinforcing pads are formed only on the exterior of the glove material, such that internal fingertip volume is substantially unaffected by the presence of the reinforcing pad.

In accordance with one embodiment, the reinforcing pads each include a plastic layer. In another embodiment, the reinforcing pads merely comprise thickened areas of the flexible glove material.

In addition to the reinforcing pads provided at the fingertips and thumb tip, a reinforcing band may be provided over the dorsal metacarpal-phalangeal joints.

The provision of the reinforcing pad along the volar sides of the dorsal ends of the glove thumb and fingers provides a reinforcement precisely where most needed, i.e., along the fingertips and thumb tips, where needle penetration or abrasion are most likely to occur. By providing reinforcing pads only in these areas, the remaining glove remains pliable and flexible to enable free and unhindered use of the hand during surgery. The reinforcing portions are preferably sufficiently thin to not substantially affect the interior volume of the glove fingertips to thereby prevent finger numbness which might otherwise occur if thick pads blocked a portion of the interior fingertip volume.

Also in accordance with the invention, methods are provided for manufacturing the improved surgical glove. In one method, a conventional glove mold is dipped into a latex liquid to coat the mold with a thin layer of latex. Then only the fingertip and thumb tip portions of the mold are redipped at an angle into the latex liquid to form a thickened layer along only the volar sides of the distal ends of the fingertips. The latex is then dried and removed from the mold to produce a surgical glove having thickened portions of latex along the finger and thumb tips.

In an alternative method, a glove mold is provided with shallow cavities formed on volar sides of distal ends of thumb or finger portions of the mold. The mold is dipped into the latex liquid to coat the mold with a layer of latex, with the shallow cavities receiving a thicker portion of the latex than remaining portions of the glove. The latex liquid is dried to form a surgical glove having thickened portions formed along the interior of the glove. The glove is then removed and inverted to reorient the thickened portions to the exterior of the glove, thereby yielding a surgical glove having one or more external reinforcing pads formed along the fingertips or thumb tip of the glove.

Alternatively, a conventional glove mold is dipped into a latex liquid to coat the mold with a first layer of latex. Then a plastic pad is mounted to a volar side of a distal end of a thumb or finger portion of the mold. The mold is redipped into the latex liquid to coat the mold with a second layer of liquid, with the second layer thereby coating the first layer and the plastic pad. The latex liquid is dried and removed from the mold to form a surgical glove.

Also alternatively, a glove mold is provided with a rib protruding from a dorsal side of a distal end of a thumb or finger portion of the mold. The rib is longitudinally aligned with the thumb or finger. The glove mold is dipped into a latex liquid to coat the mold with a first layer of latex, with the resulting layer being thinner along the rib than along remaining portions of the glove mold. The mold is then redipped into the latex up to a proximal end of the rib to coat the distal end of the thumb or finger portion of the mold with a second layer of latex. The second layer provides a thickened reinforced portion primarily along the volar side of the distal end of the glove thumb or glove finger. The latex liquid is dried and removed from the mold to produce a surgical glove. The rib portion ensures that a lesser thickness of latex is formed along the dorsal side of the reinforced fingertip. The thinner dorsal latex layer provides improved flexibility to compensate for any loss in flexibility caused by the presence of the thicker volar portion.

An alternative glove mold is provided with the thumb and fingers of the mold extending outward to allow only the thumb and fingers to be redipped into a latex bath. This allows a reinforcing layer of latex to be easily applied to only the finger and thumb tips.

Thus, the invention provides several methods for manufacturing the improved surgical glove.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 4 is a cross-sectional view of the single digit of the improved glove of FIG. 3 taken along line 4–4, but excluding the finger;

FIG. 6b is a side elevational view of the single digit of FIG. 6a;

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an improved surgical glove.

Figure 1:
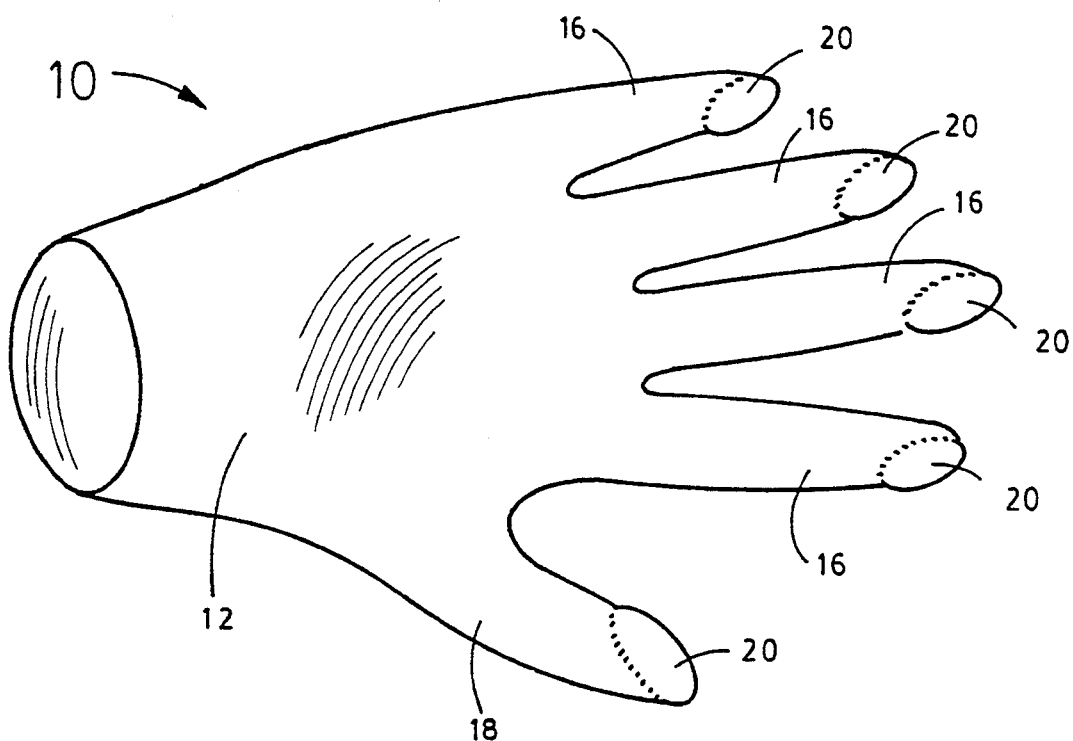
FIG. 1 is a perspective view of the volar side of an improved surgical glove constructed in accordance with an embodiment of the invention.
Figure 2:
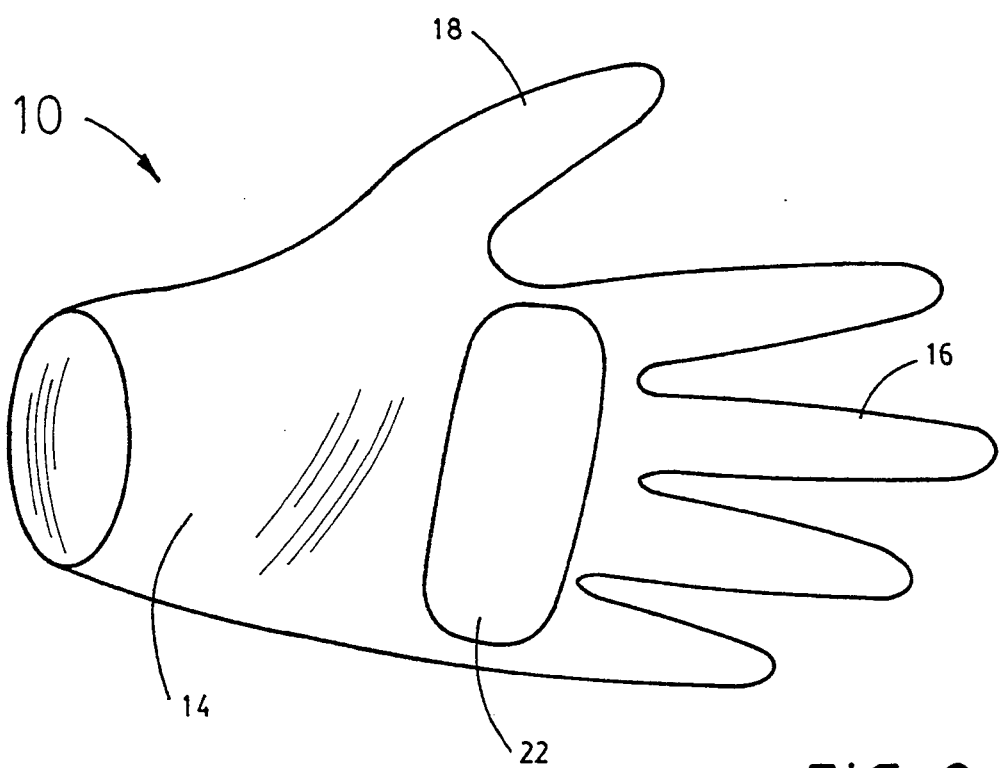
FIG. 2 is a perspective view of the dorsal side of the improved surgical glove of FIG. 1.

In FIGS. 1–4, an improved surgical glove 10 is shown. In FIG. 1, a volar side 12 of glove 10 is shown, whereas in FIG. 2, a dorsal side 14 of glove 10 is shown. Glove 10 includes four glove fingers 16 and a glove thumb 18, collectively glove digits, for receiving the fingers and thumb of a hand. In FIGS. 1 and 2, only a right-handed glove 10 is shown. The corresponding left-handed glove, a mirror image duplicate of the right-handed glove, is not shown.

Figure 3:
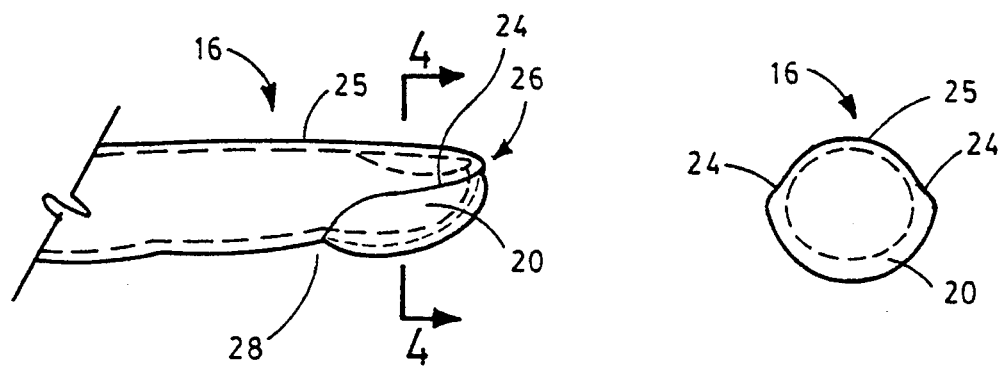
FIG. 3 is a perspective view of a single digit of the improved glove of FIG. 1 shown enclosing a finger.

Glove 10 is provided with reinforcing pads 20 along a portion of the volar and lateral aspects of glove fingers 16 and glove thumb 18. As shown in FIG. 3 by an exemplary glove finger, each reinforcing pad 20 covers the volar and lateral aspects of corresponding distal finger and thumb pulps. Pads 20 are provided to protect the finger and thumb tips from possible laceration and to reinforce the finger and thumb tips to prevent glove 10 from abrading and tearing along the finger or thumb tips. As noted above in the Summary of the Invention, the finger and thumb tips are the portions of the surgical glove most likely to be accidentally penetrated by a needle or other sharp object during surgery. Further, the finger and thumb tips are the most likely portions of the surgical glove to abrade during surgery, thereby possibly tearing. Pads 20 are thus optimally positioned for reinforcing the most vulnerable portions of the surgical glove.

In the embodiment of FIGS. 1–4, all of the digits of the glove are provided with pads 20. Although not shown, in an alternative embodiment, only the first and second fingers and the thumb include a reinforcing pad.

As shown in FIG. 2, an optional dorsal pad or band 22 is provided. Pad 22 laterally extends across a dorsal portion of glove 10 for covering the metacarpal-phalangeal joints. In use, a surgical glove is typically stretched in the vicinity of the metacarpal-phalangeal joints, thus causing a risk of tearing or abrasion. Dorsal pad 22 is optimally positioned to reinforce the metacarpal-phalangeal joints.

Preferably, glove 10 is formed from a flexible latex having conventional thickness in all areas except the reinforced portions. Pads 20 and 22 comprise thickened portions of the flexible latex. Alternatively, in an embodiment discussed below, pads 20 and 22 further include a reinforcing plastic layer.

Optimal glove flexibility is critical during any surgical procedure. If the latex of the glove is too thick and inflexible, precise manipulation of the fingers is impaired. Any hindrance to the free movement of the physician's fingers may have severe consequences during a delicate and precise surgical procedure. Further, an insufficiently flexible surgical glove causes increased fatigue in the physician's hand and fingers, a consequence of the additional force necessary to manipulate fingers within a less flexible glove. Also, numbness of the thumb and fingers is likely to occur within an insufficiently flexible surgical glove due to a lack of adequate blood supply resulting from pinching of the thumb and fingers.

The improved glove of the invention is optimally configured to provide adequate flexibility throughout the entire glove surface, while providing reinforcement along portions most vulnerable to abrasion or laceration.

As can be seen from FIGS. 3 and 4, pad 20 extends laterally along only the volar aspect of the glove finger between opposing lateral points 24. Longitudinally, pad 20 extends from fingertip 26 to a point 28 corresponding to the first joint a distal flexing crease of the finger. Thus, the pad 20 covers only the fleshy pulp of the finger and does not extend much beyond this region. Although the pad can advantageously be formed around the entire circumference of the glove fingers, the embodiment shown is preferred because the glove maintains greater flexibility.

Greater flexibility is achieved because the dorsal aspect 25 of the distal end of the glove finger is formed of conventional latex thickness. Thus the dorsal portion is thinner than the reinforced volar portion, thereby allowing fingers to flex in the dorsal direction, thus minimizing finger fatigue and improving mobility. By covering only the fleshy pulp portion of the finger with the reinforced pad, adequate flexibility of the glove is maintained while providing protection of volar tips.

Also in this regard, pad 20 may be formed on the exterior of glove 10 such that internal fingertip volume of the glove is unaffected. Alternatively, pad 20 may be formed on an interior surface of the glove with the pad being sufficiently thin to avoid substantially affecting the interior fingertip volume. A patch extending substantially into the interior of the glove would likely pinch the finger, thus hindering blood flow and producing numbness. By maintaining adequate internal fingertip volume, finger numbness is avoided.

In the embodiment of FIG. 3, for clarity glove finger 16 is shown in exaggerated size as compared to the inserted finger. In use, however, glove finger 16 fits snugly over the inserted finger.

As noted above, pad 20 and patch 22 are preferably formed as thickened latex regions. However, pad 20 and patch 22 may be formed by mounting a patch of material such as plastic to the latex of the glove. Methods for constructing these and other embodiments of the surgical glove are described with reference to FIGS. 5-14.

Latex surgical gloves are formed by dipping a glove-shaped mold into a latex bath one or more times until a suitable coating of latex adheres to the mold. The latex is dried and then removed from the mold, thus yielding a latex glove.

To improve adhesion, the mold may be initially dipped into a coagulant bath consisting of coagulation-inducing salts suspended in alcohol. Upon removal, the alcohol evaporates from the mold, leaving a thin layer of salts which cause the latex liquid to coagulate during dipping.

Figure 5:
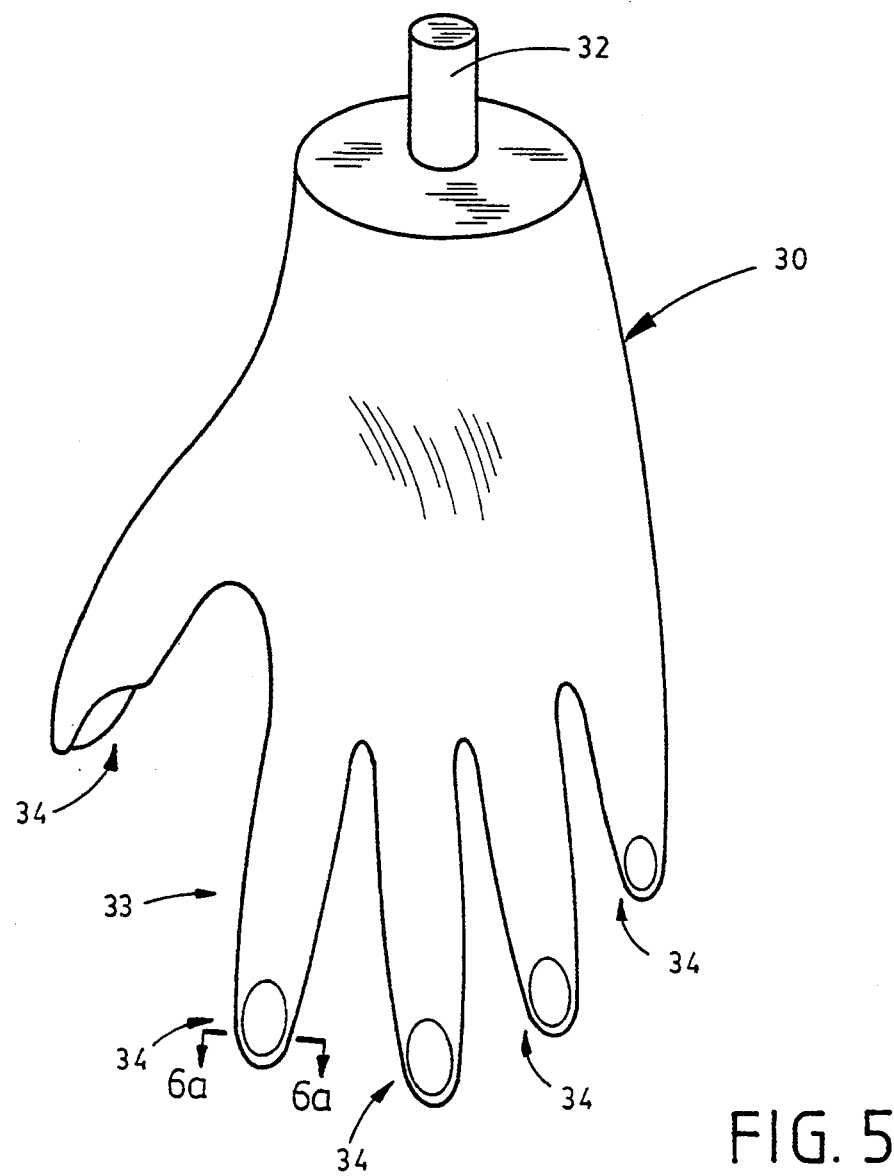
FIG. 5 is a perspective view of a glove mold provided for manufacturing the improved glove of FIG. 1.

In FIG. 5, an improved glove mold 30 is shown. In FIG. 5, the volar aspect of a right-hand glove mold is shown. The corresponding left-hand mold, a mirror image duplicate of the right-hand mold, is not shown. Glove mold 30 is constructed of a conventional material such as porcelain and includes an insertion rod or handle 32 to facilitate dipping of the mold into a latex bath (not shown).

Figure 6A:
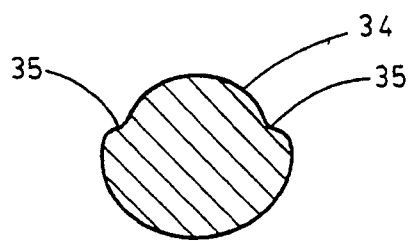
FIG. 6a is a cross-sectional view of a single digit of the glove mold of FIG. 5 taken along line 6–6.
Figure 6B:
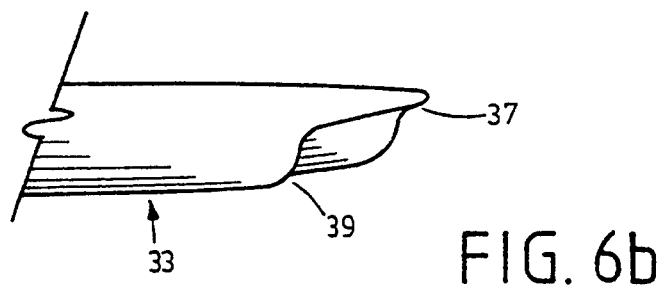

However, glove mold 30 differs from a conventional glove mold by the provision of shallow recessed regions 34 formed along the volar sides of the distal ends of the finger and thumb of the mold. An exemplary shallow recessed region 34 is shown in cross-section in FIG. 6a and in side view in FIG. 6b. Recessed portion 34 extends laterally along finger portion 33 of mold 30 between opposing lateral edges 35 (FIG. 6a) and extends longitudinally between tip 37 and a proximal end 39 (FIG. 6b).

Figure 7:
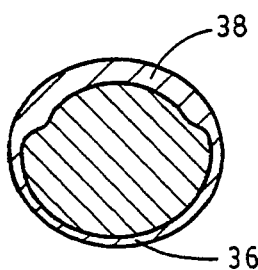
FIG. 7 is a cross-sectional view of the glove mold of FIG. 5, also taken along line 6—6, showing a latex layer formed after dipping the glove mold into a latex solution.
Figure 8:
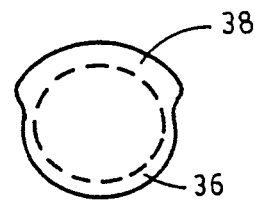
FIG. 8 is a cross-sectional view of a single digit of a resulting surgical glove formed using the glove mold of FIG. 5.

As seen in FIG. 7, after dipping glove mold 30 into a latex bath, a layer of latex 36 adheres to the mold with a greater portion 38 of latex collecting within recessed portion 34 than along unrecessed surfaces of the mold. Thus, once the latex has dried and been removed from mold 30, a surgical glove is yielded having a thickened latex portion 38 along the volar aspect of the distal end of the glove fingers and glove thumb. When initially removed from the mold, the thickened latex portion extends internally within the glove. However, the glove is then inverted to reorient the thickened latex portion to the exterior of the glove (FIG. 8), thus producing a glove with the pad on the exterior of the glove.

Thus, a suitable method for forming a surgical glove having reinforced pads includes the steps of providing a glove mold 30 with shallow recessed portions 34 along the volar aspects of the distal ends of the digits, and dipping mold 30 into a latex bath to coat the mold with a thin latex layer 36, with the resulting latex layer being thicker within shallow recessed portions 34. The method is completed by drying the latex, then removing and inverting the dried latex to yield the improved glove of the invention. A layer of coagulant salts may be initially applied to the mold to improve adhesion.

Although shown as having recessed regions along all digits, mold 30 may be configured with recessed regions on fewer of the digits, for example, only the thumb and first and second fingers.

Figure 9A:
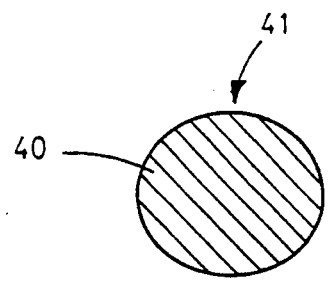
FIGS. 9a–9d provide sequential cross-sectional views of a single digit of a glove mold, showing the steps of an improved manufacturing method wherein a plastic or latex pad is enclosed between the layers of latex, with a resulting surgical glove shown in cross-section in FIG. 9e.
Figure 9B:
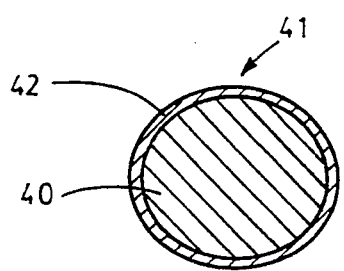
Figure 9C:
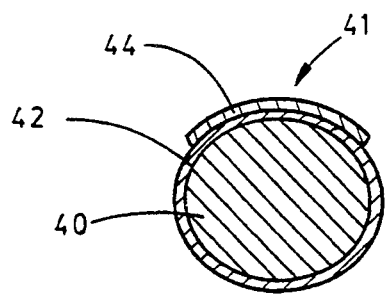
Figure 9D:
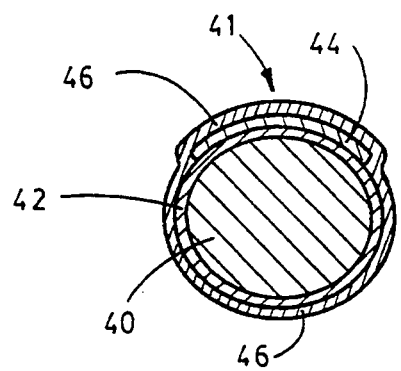
Figure 9E:
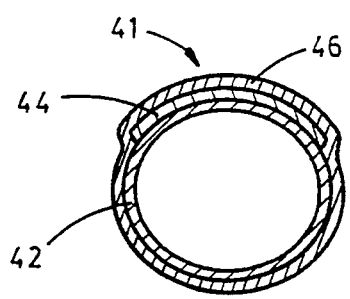
Figure 10:
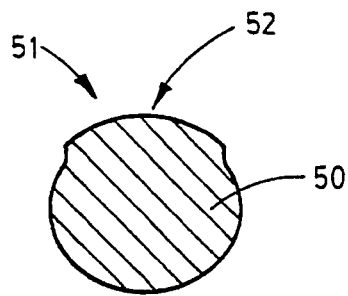
FIGS. 10a–10c provide views of an alternative glove mold showing steps of an alternative manufacturing method, with a resulting surgical glove shown in cross-section in FIG. 10d.
Figure 10:
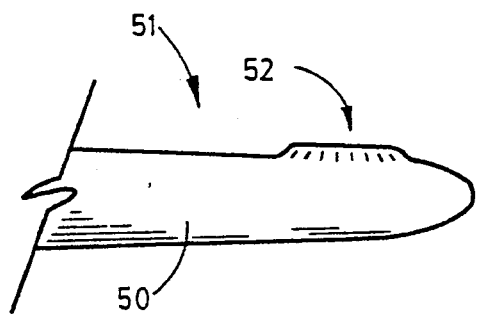
Figure 10:
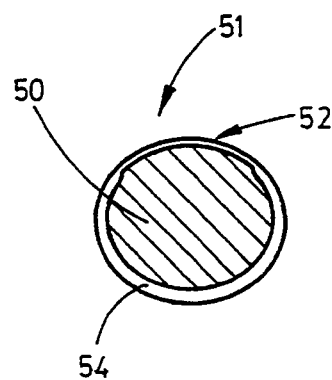
Figure 10:
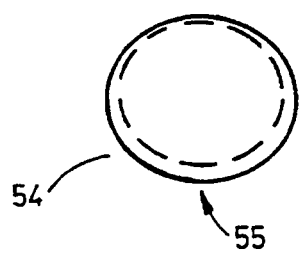

With reference to FIGS. 9a-9e, a second method for manufacturing an improved surgical glove will be described. In the second method, a conventional unmodified glove mold 40, shown in cross-section in FIG. 9a, is dipped into a latex bath to produce a first latex layer 42, as shown in FIG. 9b. Glove mold 40 is removed from the latex bath and dried. A pad 44 is then manually attached to the volar aspect 41 of the distal end of the glove mold digits. Depending upon the consistency of latex layer 42, when pad 44 is attached, an adhesive may be needed to secure pad 44 to latex layer 42. Next, glove mold 40 is redipped into the latex bath to provide a second latex layer 46 covering first latex layer 42 and pad 44. In this manner, pad 44 is enclosed within the latex of the glove. The resulting latex glove is shown in cross-section in FIG. 9e.

Preferably, glove mold 40 is initially dipped only enough times to achieve a latex layer one-half as thick as a conventional surgical glove. Thus, when the glove mold is redipped into the latex, the resulting glove has conventional latex thickness. The initial half-layer of latex may be alternatively formed by first providing a half-layer of coagulant.

Unlike the method of FIGS. 6 and 7, the resulting latex glove of the method of FIGS. 9a-9e need not be inverted. However, if desired, the glove may be subsequently inverted to reorient the pad to the interior of the glove.

Pad 44 may be constructed of any suitable material. However, it is preferred that a resilient plastic be used. One suitable plastic material is the plastic sold under the trademark "Mylar TM." Another suitable plastic is the plastic sold under the trademark "Kevlar TM." Other pad materials, including latex, can be used within the scope of the invention.

With reference to FIGS. 10a–10d, a third method of forming an improved glove will be described. A glove mold 50, shown in cross-section in FIG. 10a and in side view in FIG. 10b by an exemplary digit, is provided which is conventional in all respects, except that a thin rib 52 is formed as mounted along the dorsal aspect 51 of the distal ends of one or more of the digits of the mold. Rib 52 extends longitudinally along the digit to a proximal point 33. Rib 52 has a lateral width of, preferably, ⅛-to 3/16-inch.

Mold 50 is dipped into a latex bath a sufficient number of times to produce a latex layer of conventional thickness over most of the mold. However, with the provision of protruding rib 52, the resulting latex layer 54 has less thickness over the rib than over remaining portions of the mold, as shown in FIG. 10c.

Next, mold 50 is redipped into the latex bath only up to proximal end 53 of rib 52 (FIG. 10b) to increase the thickness of latex layer 54 around the entire distal end of the finger of the mold. Rib 52 ensures a thinner latex layer along the dorsal aspect of the distal end of the glove. Latex layer 54 is then allowed to dry, and the resulting surgical glove is removed from mold 50.

A finger of the resulting surgical glove is shown in cross-section in FIG. 10d. As can be seen from FIG. 10d, the distal end of a finger of the resulting glove has increased thickness along the volar aspect 55. The specific size, shape, and location of rib 52 may be selected to achieve a desired shape and thickness of the resulting latex glove.

Figure 11:
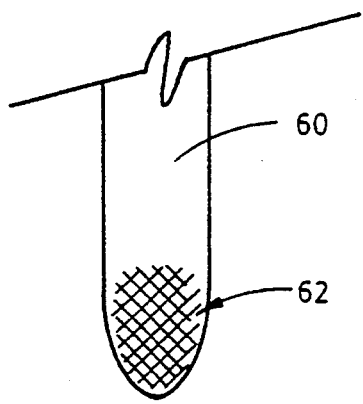
FIG. 11 is a side view of the volar side of a single digit of a glove mold showing a toughened portion formed thereon.

Another alternative glove mold embodiment is shown by way of an exemplary digit in FIG. 11. Glove mold 60 of FIG. 11 is conventional, but includes a roughened or striated surface 62 covering the volar aspect of the distal end of one or more of the mold digits. Upon dipping into a latex bath, the roughened surface 62 causes increased aggregation of the latex solution in the vicinity of the toughened portion, thus producing an increased thickness of latex at the volar side of the distal finger pulp.

Figure 12:
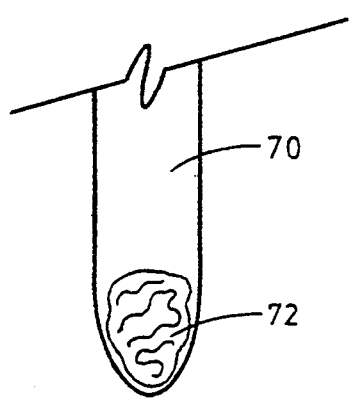
FIG. 12 is a side view of the volar side of a single digit of a glove mold showing a coagulant deposited thereon.

Alternatively, as shown in FIG. 12, rather than providing a roughened or striated portion, the glove mold may be coated with additional coagulant to cause a greater concentration of latex to adhere, again yielding a thickening of the resulting latex layer at the distal pulp of the resulting glove. In FIG. 12, a glove mold 70 is shown with a coagulant coat 72. Any suitable conventional latex coagulant may be used. The coagulant may be manually spread on the surface of a conventional mold.

Figure 13:
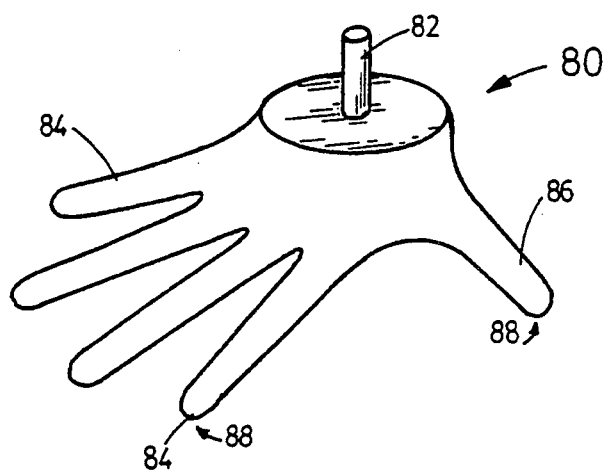
FIG. 13 is a perspective view of an alternative embodiment of a glove mold.
Figure 14:
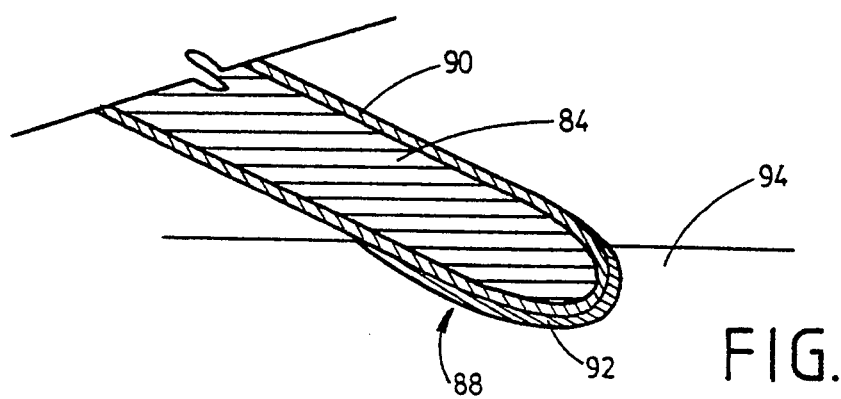
FIG. 14 is a lateral cross-sectional view of a distal end of a single digit of the glove mold of FIG. 13, shown dipped at an angle into a latex bath.

Yet another alternative glove mold embodiment is shown in FIGS. 13 and 14. Glove mold 80 is conventional in configuration, except that glove fingers 84 and glove 86 are extended outward to allow only the volar sides 88 of the glove fingers and glove thumb to be dipped into a latex bath. In other words, the fingers and thumb of the glove mold are oriented such that the tips of the fingers and thumbs all lie in a common plane. This is in contrast to a conventional glove mold, wherein the fingers and thumb are oriented in the configuration of a relaxed hand, with the volar side of the thumb pointed towards the volar sides of the fingers. In FIG. 13, the volar sides of the fingers and thumbs all point in a common direction away from the palm of the glove mold.

The outwardly-extending configuration of the digits of glove mold 80 allows only the volar sides 88 to be dipped into a latex bath to provide additional latex only along the finger and thumb tips.

In use, glove mold 80 is dipped completely into a latex bath to form an initial latex layer 90 of conventional thickness. Next, only the finger and thumb tips of mold 80 are redipped into the latex bath to provide a second layer 92 of latex along the finger and thumb tips, as shown in FIG. 14. The outwardly-extending configuration of glove mold 80 ensures that digits 84 may be dipped into the latex at an angle, allowing the second layer of latex to cover primarily the volar sides.

Although only one such digit is shown within FIG. 14, it should be understood that all five digits of glove mold 80 are simultaneously dipped by the same amount. If it were not for the extended configuration of glove mold 80, the finger and thumb tips of the mold could not simultaneously be dipped to achieve a second layer of latex only along the finger and thumb tips.

Thus, a suitable method for forming a surgical glove using the improved mold of FIGS. 13 and 14 comprises the steps of first dipping the entire mold into a latex bath to form a first layer of latex, and then redipping only the thumb and finger tips to form second layers of latex, primarily on the volar sides of the distal ends of the fingers and thumb of the mold. The latex is then allowed to dry and is removed to yield a surgical glove having reinforced portions along the finger and thumb tips. The glove may be inverted to reorient the second latex layers to the interior of the glove to ensure a smooth exterior surface.

Although not shown, reinforcing layers may be alternatively applied to the thumb and fingertips of the mold by providing five separate latex baths (not shown) having differing latex levels such that the fingers and thumb of a conventional glove mold may be dipped to form reinforcing latex layers on only the finger and thumb tips. The position and level of the individual latex baths is chosen to ensure that only the finger and thumb tips receive additional latex. Preferably, the glove mold is initially dipped into a conventional latex bath to form a latex layer over the entire glove. Then, the mold is positioned over the individual latex baths and lowered into the baths to apply additional latex to only the finger and thumb tips.

Figure 15:
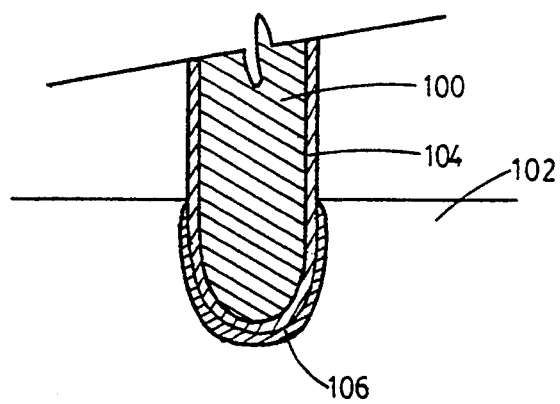
FIG. 15 is a lateral cross-sectional view of a distal end of a single digit of a glove mold, shown dipped vertically.

Although the various embodiments discussed so far primarily involve the formation of reinforcing pads primarily on only the volar sides of the distal ends of the digits of the glove, the pads may also be formed circumferentially around the entire fingertips and thumb tips. In FIG. 15, an exemplary digit of a conventional glove mold 100 is shown being dipped vertically into a latex bath 102. Initially, the entire glove mold is dipped to form a first layer 104 covering the entire mold. Next, only the ends of the digits of the mold are dipped vertically into latex bath 102 to form a second layer 106 of latex circumferentially surrounding the entire end of the digit.

The resulting surgical glove thus includes a reinforcing portion covering the entire distal ends of the fingers and thumbs to provide a greater area of protection against possible needle penetrations.

In addition to the improved glove molds and glove forming methods discussed above, any suitable glove forming method can be employed to produce a thickened pad over the distal finger and thumb pulps. For example, additional latex can be applied directly to a conventional glove to produce a thickened pad. Such can be provided by manually "painting" the additional latex onto the glove. Alternatively, various pads can be directly attached to the exterior of a conventional surgical glove. Various suitable adhesives can be employed to secure the pad to the exterior of the glove.

Metacarpal-phalangeal pad or band 22 may be formed from any of the above-described methods. For example, a glove mold may be provided with a large shallow recessed portion at the base of the digits for receiving an increased amount of latex, to thereby achieve a thickened latex pad. Alternatively, a plastic pad may be attached to the exterior of a first layer of latex, with the pad subsequently covered in a second layer of latex.

In any of the described embodiments and methods, improved surgical gloves are achieved. The gloves include reinforcing pads covering the distal finger and thumb pulps to minimize the possibility of needle penetration or abrasion. The resulting gloves are of conventional flexibility along the remainder of the glove, thus allowing sufficient mobility of the fingers, thumb, and hand.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a surgical glove composed of a thin flexible material of generally uniform thickness, the improvement comprising five reinforcing pads respectively formed only from a thickened portion of said flexible material along volar sides of distal ends of the glove thumb and glove fingers, said reinforcing pads positioned to cover substantially only the distal phalangeal finger and thumb pulps distal to the distal flexion creases of digits of a hand inserted into said glove; and a reinforcing band formed from a thickened portion of said flexible material extending along a dorsal portion of the glove for covering substantially only the metacarpal-phalangeal joints.

* * * * *